United States Patent [19]
Matsuda et al.

[11] Patent Number: 5,994,326
[45] Date of Patent: Nov. 30, 1999

[54] ANTI-ATOPIC DERMATITIS COMPOSITION

[75] Inventors: Michio Matsuda, Kushiro; Sechiko Takeuchi, Hiroshima; Taizo Nagura, Obihiro; Tsutomu Aritsuka, Obihiro; Kouji Sayama, Obihiro, all of Japan

[73] Assignee: Nippon Tensaiseito Kabushiki Kaisha, Tokyo, Japan

[21] Appl. No.: 09/132,267

[22] Filed: Aug. 11, 1998

[30] Foreign Application Priority Data

Mar. 10, 1998 [JP] Japan .................................. 10-075006

[51] Int. Cl.⁶ .................................................. A61K 31/715
[52] U.S. Cl. ........................................................ 514/61
[58] Field of Search ................................................ 514/61

[56] References Cited

FOREIGN PATENT DOCUMENTS 59-067214  4/1984  Japan .
09154535  6/1997  Japan .

OTHER PUBLICATIONS

Truss, C.O., "The Missing Diagnosis, Second Edition" 'The Clinical Picture,' *The Missing Diagnosis Inc.* pp. 33–37 (1982).

Truss, C.O., "The Missing Diagnosis, Second Edition" The Role of Candida Albicans in Human Illness, *The Missing Diagnosis Inc.* pp. 155–165 (1982).

Crook, W.G., "The Yeast Connection, A Medical Breakthrough," *Vintage Books* pp. 9–14 (1986).

Brostoff, J., et al., "Food Allergy and Intolerance," 'Kroker, G.F., "Chronic Candidiasis and Allergy,"' *Bailliere Tindall* pp. 854–870 (1987).

Matsuda M. et al., "Allergy in Clinics," 11:768–772 (1991).

Makino, S., "Guideline for Treatment of Allergic Diseases," *Life Science Medica* pp. 141–145 (1995).

"Health Life Business for Food," Sep. 15, 1997.

*Primary Examiner*—Phyllis G. Spivack
*Attorney, Agent, or Firm*—Browdy and Neimark

[57] ABSTRACT

The present invention relates to an anti-atopic dermatitis composition containing raffinose as the effective ingredient that can be satisfactorily administered to babies and infants for a long term.

11 Claims, 3 Drawing Sheets

ANTI-ATOPIC DERMATITIS COMPOSITION

DETAILED DESCRIPTION OF THE INVENTION

1. Field of the Invention

The present invention relates to an anti-atopic dermatitis composition; more specifically, the present invention relates to a composition for preventing or therapeutically treating atopic dermatitis, the composition containing raffinose an (oligosaccharide) as the effective ingredient.

2. Description of Prior Art

A concept has been presented in recent years such that various symptoms and diseases are triggered through canditoxin by the over growth of candida which is a fungus commonly present in gastro-intestinal tract such as intestinal tract. It has also been reported that these symptoms and diseases are ameliorated by the combination treatment of oral administration of anti-fungal agents and the elimination of candida growth factors (sugar, fruits, and alcohol). The condition is variously is called chronic candidiasis (C. O. Truss, 1983), yeast connection (W. G. Crook, 1984), chronic candidiasis sensitivity syndrome (G. F. Krocker, 1987) and the like.

Since Matsuda et al. have reported domestically in Japan that the above noted combination treatment is also effective for 70 to 80% of relatively severe patients with atopic dermatitis (Michio Matsuda and Makoto Takahashi, Allergy in Clinics, Vol.56, pp.768–772, 1991), such combination treatment has been introduced into the Guideline for Treatment of Allergic Diseases (Michio Matsuda, Guideline for Treatment of Allergic Diseases, edited by Souhei Makino, Life Science Medica, Tokyo, 1993).

Alternatively, oligosaccharides are types of sugars, composed of 2 to 10 monosaccharides, which have a property to proliferate bifidobacteria and thereby help intestinal functions. Recently, oligosaccharides has been in Japan used in sour milk drinks, refreshing drinks and canned coffee and the like.

As one type of oligosaccharide, raffinose is assimilated with bifidobacteria and lactobacilli and is a trisaccharide widely distributed in plants. Raffinose has a white needle crystal structure and is contained in beet and the like. It is believed that raffinose induces the growth of bifidobacteria and suppresses the growth of *Escherichia coli* and Welsh bacteria.

However, it has never been known that raffinose is effective for preventing and treating atopic dermatitis or it has absolutely never been reported that the action is verified at clinical tests for human subjects, including in vitro experiments and in vivo experiments in experimental animals.

PROBLEMS TO BE SOLVED BY THE INVENTION

Because the symptoms of allergic diseases, particularly atopic dermatitis are apparently overt, the diseases have drawn concerns; and additionally, patients with atopic dermatitis have increased in recent years. In such current circumstances, the countermeasures against there diseases have been needed strongly.

MEANS FOR SOLVING THE PROBLEMS

Figure 1:
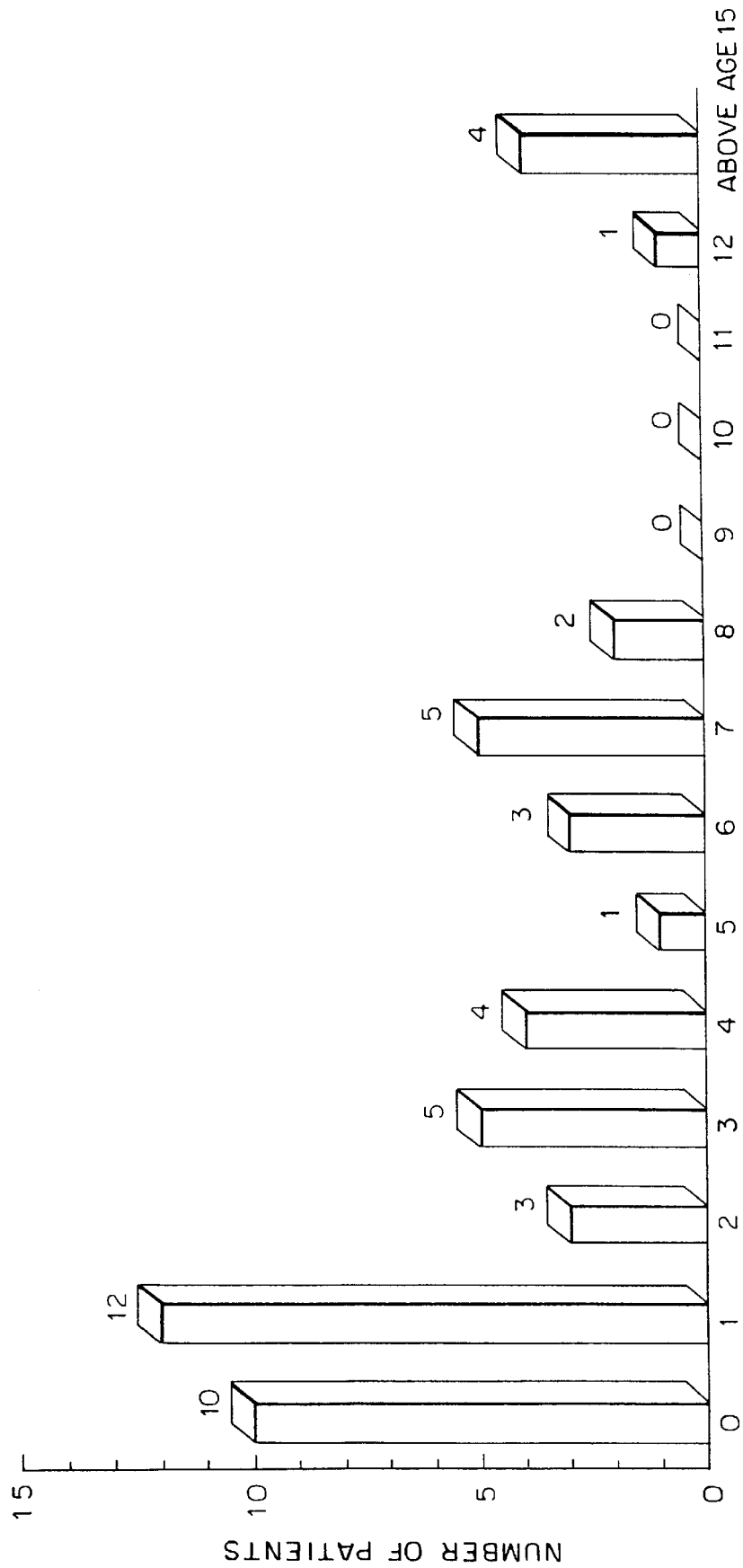
FIG. 1 is an age distribution figure of clinical test subjects.
Figure 2:
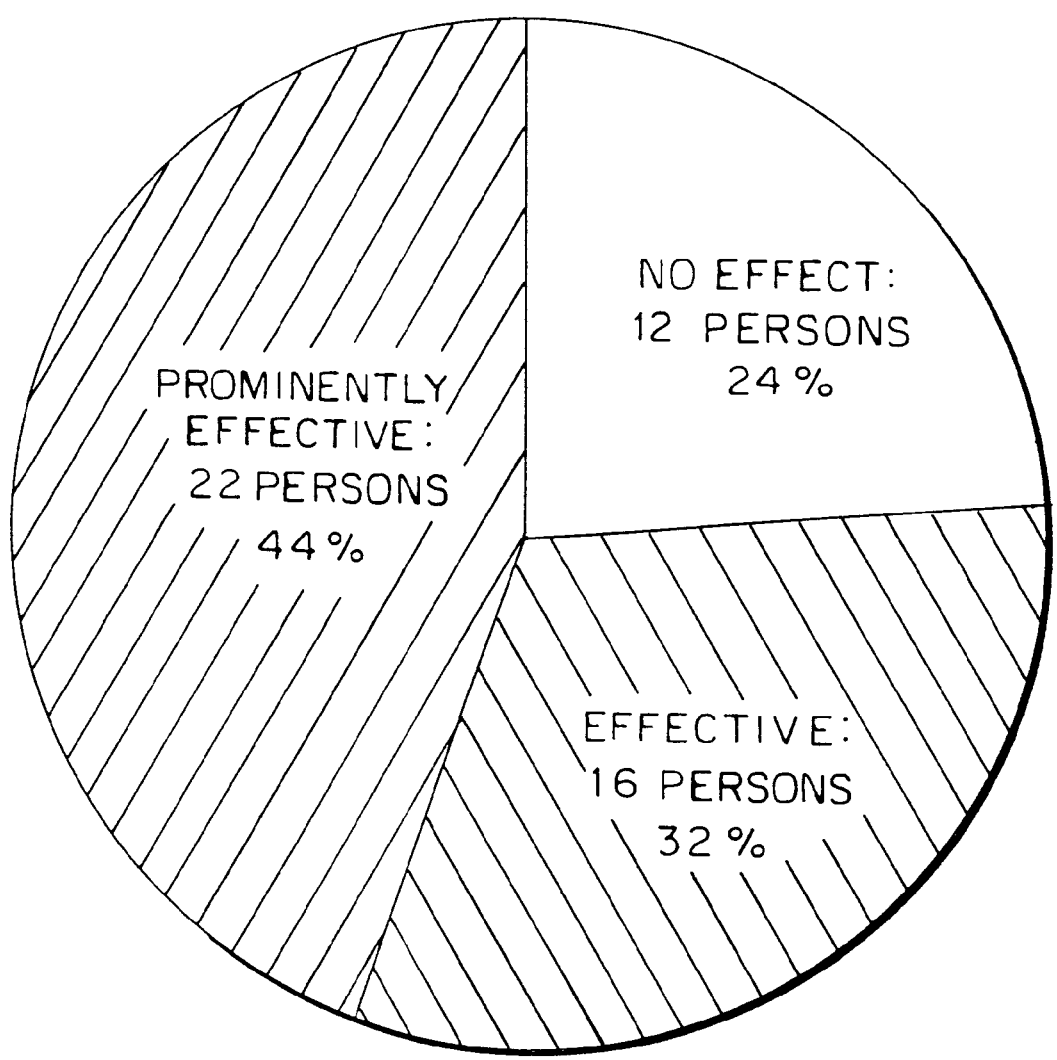
FIG. 2 shows the effects of raffinose.

So as to attain the object, the present inventors have made investigations from various aspects. For the purpose of developing an anti-atopic dermatitis composition with higher safety and ready oral administration from the standpoint that the average age of the patients is relatively low and the therapeutic treatment thereof requires a long term, the inventors have eventually focused their attention to products from natural origin with less side effects.

Among a great number of natural products, the inventors have firstly focused their attention on oligosaccharides, particularly raffinose, to conduct a clinical test by actually administering raffinose orally to patients with atopic dermatitis, assuming that raffinose might have the same effects as those of conventional anti-fungal agents orally given. The efficacy has been verified in human subjects in a practical sense. After further investigations, the present invention has been achieved.

More specifically, the present invention relates to an anti-atopic dermatitis composition containing raffinose as the effective ingredient. In accordance with the present invention, an excellent anti-atopic dermatitis composition with greater safety can be provided, which can be given orally.

The present invention will now be described below.

The anti-atopic dermatitis composition of the present invention is formulated by adding routine inorganic or organic carriers or pharmaceutical excipients into the effective ingredient raffinose and then preparing the mixture into oral preparations or parenteral preparations such as external preparations in the forms of solids, semi-solids or fluids.

The oral preparations include for example tablets, capsules, granules, powders, syrups, and gargles. These various formulations can be formulated by using the principal agent, together with known routine auxiliary agents in the field of pharmaceutical technology, such as excipients, binders, disintegrators, lubricants, flavor, dissolution auxiliary agents, suspending agents, coating materials and the like.

The preparations can be administered at a dose of 0.5 g to 15 g /day/adult, preferably 3 to 10 g/day/adult, but the dose varies, depending on the symptoms, age, body weight, and dosage and formulation.

Because the effective ingredient of the present invention is derived from natural origin and is used as food, no toxicity concern will occur. No acute toxicity is observed even at an oral dose of 500 mg/day in rats. Hence, a higher amount above the range described above may satisfactorily be used. Because raffinose is a slightly digestible saccharide, however, raffinose at a dose of 10 g/day or more may induce osmotic diarrhea in some individuals.

As to the effective ingredient, most preferably, purified raffinose should be administered, but use may be made of raffinose at a more or less low purification degree, such as syrup processed materials as by-products from the production process of beet sugar.

Examples of the present invention will now be described hereinbelow.

EXAMPLE 1

Raffinose was administered to patients with atopic dermatitis. The clinical effects were verified as follows.

1. Subjects of Clinical Test

Among atopic dermatitis patients visiting our hospital (Fumi-zono Matsuda Dermatology Hospital), 50 of the patients were noted on the diet diary that they ate too high a quantity of sweets, fruit and alcohol so they were advised to adopt a diet without these foods. However, no sufficient amelioration of atopic dermatitis was observed in them (23 males and 27 females; age 0 to 23 years old of mean age 4.32 years old) The patients were enrolled into a clinical test (FIG. 1).

2. Procedures of Clinical Test

While enforcing them to continue the elimination of sweets, fruit and alcohol from their diet, raffinose was administered to them at the following doses for one to 2 weeks according to Takeuchi's method. Then, the amelioration of dermatitis and itching was observed. Raffinose was administered up to 6 weeks. As to combination agents, the formulations indicated prior to the test were continued, but no additional formulation was prescribed after the initiation of the test. In some of the patients, furthermore, the dose of the agents was reduced or the dosing was discontinued, depending on the amelioration, after the initiation of the test.

The raffinose dose was as follows. 1.0 g/day for infants, 1.0 g/day for one-year olds, 2.0 g/day for 3-year olds, 3.0 g/day for 6-year olds, and 6.0 g/day for adults.

3. Results of Clinical Test

Among the 50 subjects of the clinical test, prominent efficacy (almost complete disappearance of dermatitis) was observed in 22 (44%); efficacy (erythema, infiltration and reduced itching) was observed in 16 (32%); no efficacy was observed in 12 (24%); and exacerbation was observed in 0 (0%). Thus, the efficacy including prominent efficacy and efficacy was observed in 38 (76%) out of 50. No substantial side effect was observed (diarrhea occurred in one case, but the reduction of the single dose could eliminate diarrhea).

Figure 3:
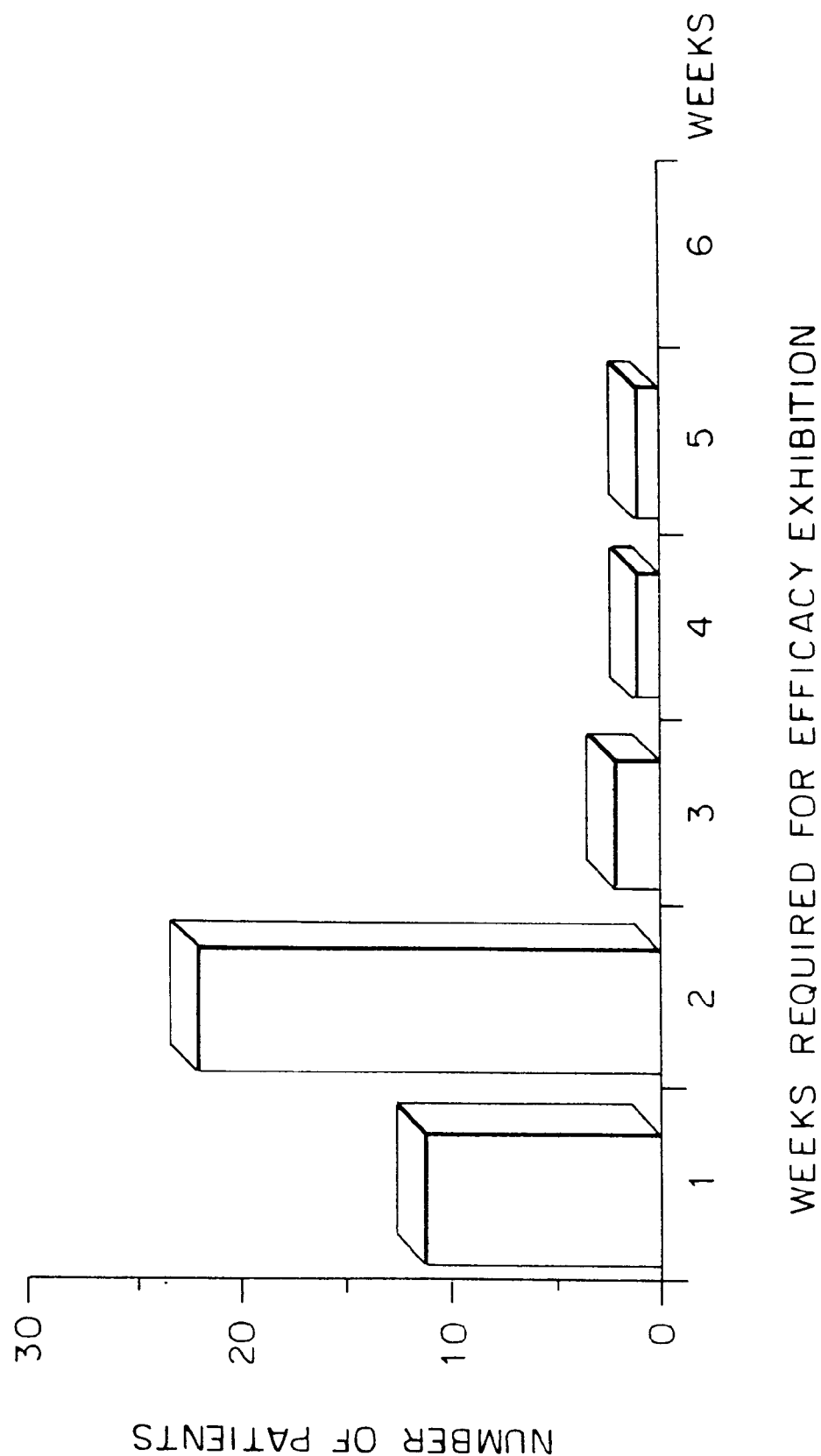
FIG. 3 shows the weeks required for the exhibition of raffinose effect.

The number of weeks for the effect to be exhibited was one to 5 weeks, with 1.92 weeks on average (FIG. 3).

The types of dermatitis ameliorated with raffinose in such manner are shown in Table 1. As apparently shown in the outcome, no specific difference was observed between the dermatitis types in the patients with prominent efficacy and efficacy and the patients with no efficacy. In the patients with prominent efficacy and efficacy, the highest response was observed in patients with patchy distributed erythematosquamous plaque on the trunk.

In 3 out of the 12 patients with no efficacy, the dermatitis was ameliorated by changing raffinose to oral administration of anti-fungal agent amphotericin B.

TABLE 1

Dermatitis types ameliorated by raffinose

|  | Facial diffuse erythema | Periorbial erythema | Perioral erythema | Nummular dermatitis like eruption | Erythema on neck and chest | Scale on whole body | Itching | Constipation |
|---|---|---|---|---|---|---|---|---|
| No efficacy | 4 | 1 | 2 | 6 | 0 | 0 | 0 | 0 |
| Efficacy | 1 | 3 | 4 | 11 | 0 | 0 | 0 | 1 |
| Prominent efficacy | 1 | 2 | 3 | 12 | 2 | 1 | 1 | 1 |

Perioral erythema; facial erythematosus except mouth and nose
Nummular dermatitis like eruption; patchy distributed erythematosquamous plaque on the trunk distributed in an island pattern on body.

The effects of raffinose (in all the cases) are shown in Tables 2 and 3. In the table of raffinose effect No. 1, 0 represents no effect; 1 represents effective; and 2 represents prominently effective. In the column of dermatitis type 2, individual symbols represent as follows; A represents Facial diffuse erythema face, B represents Periorbital erythema around eye; C represents Perioral erythema; D represents Nummular dermatitis like eruption; E represents Erythema on neck and chest; F represents Scale on whole body; G represents Itching; and G represents Constipation.

TABLE 2

Effect of Raffinose (in all cases) 1

| case | sex | age | effect (1) | dermatitis type (2) | weeks before exhibition of effect | side effects |
|---|---|---|---|---|---|---|
| 1 | male | 0 | 0 | C |  | — |
| 2 | male | 0 | 0 | D |  | — |
| 3 | male | 0 | 0 | D |  | — |
| 4 | male | 1 | 0 | D |  | — |
| 5 | male | 1 | 0 | D |  | — |
| 6 | male | 3 | 0 | A |  | — |
| 7 | female | 3 | 0 | D |  | — |
| 8 | male | 4 | 0 | C,D |  | — |
| 9 | female | 6 | 0 | A |  | — |
| 10 | male | 12 | 0 | A |  | — |
| 11 | female | 17 | 0 | A |  | — |
| 12 | female | 23 | 0 | B |  | — |
| 13 | female | 0 | 1 | C | 1 | — |
| 14 | female | 0 | 1 | D | 1 | — |
| 15 | femaie | 0 | 1 | D | 1 | — |
| 16 | female | 0 | 1 | D | 3 | — |
| 17 | female | 1 | 1 | D | 2 | — |
| 18 | female | 1 | 1 | C, D | 2 | — |
| 19 | male | 1 | 1 | D | 2 | — |
| 20 | female | 1 | 1 | B | 2 | — |
| 21 | female | 1 | 1 | D | 2 | — |
| 22 | female | 3 | 1 | B, H | 2 | — |
| 23 | male | 4 | 1 | C | 2 | — |
| 24 | male | 5 | 1 | C, D | 3 | — |
| 25 | female | 6 | 1 | B, D | 5 | — |

TABLE 3

Effect of Raffinose (in all cases) 2

| case | sex | age | effect (1) | dermatitis type (2) | weeks before exhibition of effect | side effects |
|---|---|---|---|---|---|---|
| 26 | male | 7 | 1 | D | 2 | — |
| 27 | male | 8 | 1 | D | 1 | — |
| 28 | male | 18 | 1 | A | 2 | — |
| 29 | female | 0 | 2 | E | 1 | — |
| 30 | male | 0 | 2 | D | 2 | — |
| 31 | male | 0 | 2 | D | 2 | — |
| 32 | male | 1 | 2 | D | 1 | — |
| 33 | female | 1 | 2 | C | 1 | — |
| 34 | male | 1 | 2 | D | 1 | — |
| 35 | male | 1 | 2 | D | 2 | — |
| 36 | female | 1 | 2 | D | 2 | — |
| 37 | female | 2 | 2 | D | 2 | — |
| 38 | female | 2 | 2 | D,H | 3 | — |
| 39 | male | 2 | 2 | D | 4 | — |
| 40 | female | 3 | 2 | F | 2 | — |
| 41 | male | 3 | 2 | D | 2 | — |
| 42 | male | 4 | 2 | D | 2 | — |
| 43 | male | 4 | 2 | G | 2 | diarrhea |
| 44 | male | 6 | 2 | D | 1 | — |
| 45 | female | 7 | 2 | A | 1 | — |
| 46 | female | 7 | 2 | B | 1 | — |
| 47 | female | 7 | 2 | C | 2 | — |
| 48 | female | 7 | 2 | E | 2 | — |
| 49 | female | 8 | 2 | D | 2 | — |
| 50 | female | 23 | 2 | B | 2 | — |

As apparently shown above, the efficacy of raffinose was observed at 76% (effective in 32% and prominently effective in 44%). Diarrhea was observed only in one case among the 50 cases, but the symptom disappeared after the reduction of the single dose; side effects were never observed or were very light. Thus, it was verified at the clinical tests that raffinose be extremely effective for ameliorating atopic dermatitis.

In the results as to the efficacy of raffinose (in all the cases), the formulation for cases 5, 8 and 9 among the cases with no efficacy of raffinose was changed to an oral anti-fungal agent. Thus, the amelioration was attained. It was demonstrated that the term required for the exhibition of raffinose was similar to the term required for the treatment with an oral anti-fungal agent nystatin (supra; Michio Matsuda, Guideline of Treatment of Allergic Diseases). No herxheimer phenomenon specific to the use of anti-fungal agents was observed.

As mentioned above, it was verified that the treatment with raffinose is safer with very less side effects, than the treatment with known anti-fungal agents such as nystatin. Therefore, the composition of the present invention is not only effective for directly treating atopic dermatitis but also effective as functional food of a food and drink type for the purpose of prophylaxis and care after treatment. For types of dermatitis responded to raffinose, raffinose is effective or prominently effective, frequently for patchy distributed erythematosquamous plaque on the trunk.

EXAMPLE 2

Four hundred parts (400 parts) by weight of crystal glucose, 10 parts by weight of raffinose, 7 parts by weight of citric acid, 7 parts by weight of Na-caseinate, 5 parts by weight of ascorbic acid, and 3 parts by weight of hardened oil were used to formulate an anti-atopic dermatitis tablet in a routine manner.

EXAMPLE 3

Fifty parts (50 parts) by weight of raffinose, 20 parts by weight of purified calcium carbonate, 178 parts by weight of lactose, and 2 parts by weight of magnesium stearate were mixed together, and the resulting mixture was filled at 250 mg into capsule No.1 which was an anti-atopic dermatitis capsule containing 50 mg raffinose per one capsule.

EFFECTS OF THE INVENTION

In accordance with the present invention, raffinose can exhibit excellent anti-atopic dermatitis effect, so that atopic dermatitis can be prevented and therapeutically treated effectively. Because the composition of the present invention is highly safe, the composition can be administered to babies and infants in a safe manner and for a prolonged term, so that the composition can be used in the form of a drink and food type for a long term.

What is claimed is:

1. Anti-atopic dermatitis composition containing raffinose as the effective ingredient and a pharmaceutically acceptable carrier, said composition being free of *Bacillus subtilis* Natto, unpolished rice powder and lactic acid bacteria, said raffinose being present in a unit dose amount sufficient to provide an anti-atopic dermatitis effect.

2. An anti-atopic dermatitis composition according to claim 1, wherein the composition is a type of pharmaceutical product.

3. An anti-atopic dermatitis composition according to claim 1, wherein the composition is a type of food or drink, and wherein said pharmaceutically acceptable carrier comprises at least one food or drink component.

4. An anti-atopic dermatitis composition according to claim 1, wherein said effective ingredient consists essentially of said raffinose.

5. A method for preventing or treating atopic dermatitis which comprises administering to a person in need thereof a composition comprising raffinose as an active ingredient in an amount effective for preventing or treating atopic dermatitis.

6. A method according to claim 5, wherein said active ingredient consists essentially of said raffinose.

7. A method according to claim 5, wherein said composition is a pharmaceutical composition in a unit dosage form, said pharmaceutical composition further comprising a pharmaceutically acceptable carrier.

8. A method according to claim 5, further comprising simultaneously modifying the diet of said person to reduce or eliminate sweets, fruit and alcohol.

9. A method according to claim 5, wherein said composition is substantially free of *Bacillus subtilis* Natto, unpolished rice powder and lactic acid bacteria.

10. A method according to claim 5, wherein said composition is a food or drink composition.

11. A method for preventing or treating atopic dermatitis which comprises administering to a person in need thereof raffinose in an amount effective for preventing or treating atopic dermatitis.

* * * * *